United States Patent [19]

Niewisch

[11] Patent Number: 5,324,932
[45] Date of Patent: Jun. 28, 1994

[54] ARRANGEMENT FOR OPTICAL FIBER MEASURING DEVICES USING DETACHABLE CONNECTOR WITH HYBRID CABLE

[75] Inventor: Joachim Niewisch, Nürnberg, Fed. Rep. of Germany

[73] Assignee: Siemens Aktiengesellschaft, München, Fed. Rep. of Germany

[21] Appl. No.: 69,634

[22] Filed: Jun. 1, 1993

[30] Foreign Application Priority Data

Jun. 2, 1992 [DE] Fed. Rep. of Germany ....... 4218170

[51] Int. Cl.⁵ .................................................. G02B 5/14
[52] U.S. Cl. .................................... 250/227.21; 359/54
[58] Field of Search ............... 250/227.21; 359/12, 359/44, 54, 59, 71

[56] References Cited

U.S. PATENT DOCUMENTS

| | | | |
|---|---|---|---|
| 3,455,625 | 7/1969 | Brumley et al. | 385/54 |
| 4,184,739 | 1/1980 | d'Auria et al. | 385/54 |
| 4,588,886 | 5/1986 | Snider | 250/227.21 |
| 4,591,712 | 5/1986 | Thalmann | 250/227.21 |
| 4,737,624 | 4/1988 | Schwarte | 250/227.21 |
| 4,766,306 | 8/1988 | Bichsel et al. | 250/227.21 |
| 5,036,194 | 7/1991 | Hazel | 250/227.21 |

FOREIGN PATENT DOCUMENTS 3833131 4/1990 Fed. Rep. of Germany .

Primary Examiner—David C. Nelms
Assistant Examiner—Stephone B. Allen
Attorney, Agent, or Firm—Kenyon & Kenyon

[57] ABSTRACT

An arrangement for an optical measuring device wherein a detachable plug-in connector is provided to optically couple a sensing device to a transmitter and to a receiver. In this arrangement, a transmitting bundle extending from the transmitter and a receiving bundle extending from the receiver are combined in a single hybrid cable whose end is optically coupled to a corresponding end of a sensing cable extending from a sensing device. To prevent light transported by the transmitting bundle from being reflected onto the receiving bundle, the respective bundles are separated from one another within the hybrid cable by a distance at least as wide as the diameter of any single fiber of the transmitting bundle or the receiving bundle.

14 Claims, 1 Drawing Sheet

ARRANGEMENT FOR OPTICAL FIBER MEASURING DEVICES USING DETACHABLE CONNECTOR WITH HYBRID CABLE

BACKGROUND OF THE INVENTION

The present invention is directed to an arrangement for optical fiber measuring devices. More specifically, the present invention is directed to an arrangement for optical fiber measuring devices wherein a sensing device is optically coupled to a transmitter and to a receiver through respective optical fiber bundles.

Optical fiber measuring devices offer distinct advantages over other types of measuring systems. Unlike electrical measuring systems, for instance, optical fiber measuring devices are insensitive to electromagnetic irradiation. Additionally, optical fiber measuring devices permit measurements to be made free of electrical potential and dissipation heat. Optical fiber measuring devices are thus particularly well-suited to medical technology applications, such as measuring a patient's pulse and respiration in the high-frequency field of a nuclear spin tomograph.

German Provisional Patent 38 33 131 discloses a photoelectric pulse recorder having an optical fiber sensing element that is optically coupled to a transmitter and a receiver by an optical fiber bundle housed in an optical fiber cable. This fiber bundle is integrally cast at one of its ends in the sensing element, such that a cross-section of the fiber bundle terminates at the application surface of the sensing element, with the longitudinal axis of the fiber bundle perpendicular to the application surface. The other end of the fiber bundle is firmly coupled to a plug connector, in which the transmitter and the receiver are also arranged. In the plug connector, the fiber bundle fans out into a transmitting bundle and a receiving bundle, leading to the transmitter and the receiver, respectively. The plug connector is electrically connected to an operating unit.

In known optical fiber measuring devices such as the pulse recorder described above, the sensing element is undetachably connected to the transmitter and the receiver; however, in many applications a detachable connection is desirable. For example, when measuring the pulse of a patient in a nuclear spin tomograph, it would be beneficial to have a detachable plug-in connector between a fiber bundle leading to a sensing element affixed to the patient and two optical fiber bundles installed in a support, namely a transmitting bundle and a receiving bundle. A requirement for any such configuration is that light transported by the transmitting bundle and reflected off the break at the connection must not be received by the receiving bundle; otherwise, light from the optical transmitter will create an interfering offset at the optical receiver. A further requirement for any such configuration is that the plug-in connector be easy to manufacture and maintain.

SUMMARY OF THE INVENTION

The present invention provides a detachable plug-in connector for optical fiber measuring devices that eliminates any interfering offset that might otherwise be caused by the reflection of light at the junction of optical fiber bundles. A transmitting bundle and a receiving bundle, both comprising a plurality of optical fibers, are combined into a single hybrid cable, whose end is optically coupled to one end of a sensing cable, also comprising a plurality of optical fibers, by the detachable plug-in connector. To prevent light transported by the transmitting bundle from being reflected onto the receiving bundle, the transmitting bundle is arranged within the hybrid cable at a predetermined distance away from the adjacent receiving bundle. The resulting separation between any two transmitting and receiving fibers is at least as large as the diameter of any single fiber.

In one embodiment of the present invention, the desired separation is attained by a crosspiece positioned in the hybrid cable such that the transmitting bundle is on one side of the crosspiece and the receiving bundle is on another side of the crosspiece. In a second embodiment, the transmitting bundle and the receiving bundle are arranged in a substantially coaxial fashion within the hybrid cable, with the respective bundles separated from one another by an internal cladding that surrounds the interior bundle.

To achieve optical connectivity between the hybrid cable and the sensing cable, an embodiment of the present invention contemplates that an end of the hybrid cable and an end of the sensing cable each have a circular cross-section of substantially equal size. The corresponding ends of the hybrid cable and the sensing cable are secured in respective rotationally symmetric plug connectors, which may be inserted into the opposite ends of a hollow cylindrical centerpiece up to a limit stop. The plug connectors and the centerpiece can be easily manufactured as simple lathed parts. The end faces of the plug connectors preferably terminate flush with the ends of the respective cables, and therefore can be cleaned quite easily. Additionally, a screw thread or a simple snap fastener may be provided to firmly attach each plug connector to the centerpiece.

DETAILED DESCRIPTION

Figure 1:
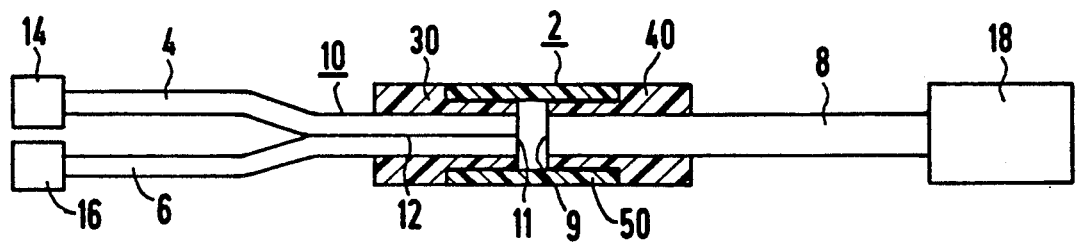
FIG. 1 depicts an optical measuring arrangement comprising a detachable plug-in connector according to the present invention.
Figure 2:
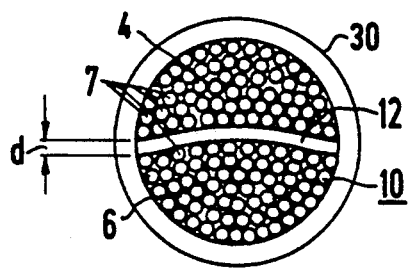
FIG. 2 shows a cross-sectional view of a hybrid cable according to the present invention, wherein the transmitting bundle and the receiving bundle are separated by a crosspiece of width d.

FIG. 1 depicts an arrangement for an optical fiber measuring device according to the present invention. An optical transmitter 14, an optical receiver 16, and an optical sensing device 18 are provided. Connected to the transmitter 14 is a transmitting bundle 4, to the receiver 16 is a receiving bundle 6, and to the sensing device 18 is a sensing cable 8, comprising a sensing bundle. Each of these bundles contains a plurality of optical fibers. The transmitting bundle 4 and the receiving bundle 6 converge in a common optical fiber cable at a point distant from the transmitter 14 and the receiver 16, forming a hybrid cable 10. The hybrid cable 10 is arranged at its end 11 in a rotationally symmetric plug connector 30, and consequently exhibits a circular cross-section, as shown in FIG. 2. Referring to both FIG. 1 and FIG. 2, to prevent light emanating from the transmitter 14 from being reflected onto the receiving bundle 6, the transmitting bundle 4 and the receiving bundle 6 are separated from one another within the hybrid cable 10, at least in the area of the end 11, by a crosspiece 12 which terminates with the cladding of the hybrid cable 10 or with the inner surfaces of the plug connector.

Figure 4:
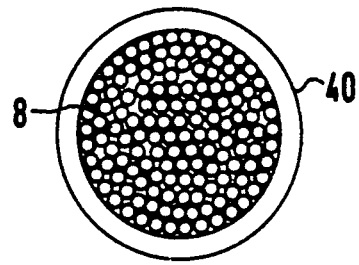
FIG. 4 shows a cross-sectional view of a sensing cable according to the present invention.

At its end 9 distant from the sensing device 18, the sensing cable 8 is arranged in a rotationally symmetric plug connector 40, and consequently exhibits a circular cross-section, as shown in FIG. 4. The plug connectors 30 and 40 can be inserted into a hollow cylindrical centerpiece 50, whose inside diameter is substantially equal to the outside diameter of each of the plug connectors 30 and 40. Thus, the centerpiece 50 and the two plug connectors 30 and 40 form a detachable plug-in connector 2, in which the cross-sectional area of the end 11 of the hybrid cable 10 is arranged parallel to the cross-sectional area of the end 9 of the sensing cable 8, with the centers of the two cross-sections being arranged on an axis perpendicular to both cross-sections and the two ends 9 and 11 are optically coupled to one another.

Figure 3:
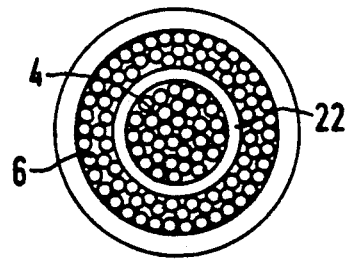
FIG. 3 shows a cross-sectional view of a hybrid cable according to the present invention, wherein two fiber bundles are arranged coaxially within the hybrid cable, with the individual fiber bundles separated by an internal cladding.

FIG. 2 and FIG. 3 depict two possible ways to separate the fiber bundles within the hybrid cable 10 according to the present invention.

In the embodiment shown in FIG. 2, the end 11 of the hybrid cable 10 that is set in the plug connector 30 is depicted in cross-section. The transmitting bundle 4 and the receiving bundle 6 are separated from one another by a crosspiece 12. The crosspiece 12 is at least as wide as the diameter of any single fiber 7 in the bundles, to prevent light transported by the transmitting bundle 4 from being reflected off the diametrically opposing sensing cable 8 and onto adjacent fibers of the receiving bundle 6. Preferably, all of the individual fibers 7 have the same diameter. In cases where the individual fibers 7 vary in thickness, the crosspiece 12 should be at least as wide as the largest diameter of these fibers. The width of the crosspiece 12 determines the minimum distance d between one fiber of the transmitting bundle 4 and a neighboring fiber of the receiving bundle 6.

In the specific embodiment shown in FIG. 3, the transmitting bundle 4 and the receiving bundle 6 are arranged coaxially, and are separated from one another by means of a hollow, cylindrical internal cladding 22. It will be apparent to those skilled in the art that either the transmitting bundle 4 or the receiving bundle 6 can be positioned inside the internal cladding 22.

The rotationally symmetric end 9 of the sensing cable 8 set in the plug connector 40 is depicted in cross-section in FIG. 4. Preferably, the end 9 of the sensing cable 8 and the end 11 of the hybrid cable 10 have substantially the same diameter.

Since a single sensing cable 8 is provided for transmitting light to and from the sensing device 18, and because it is therefore immaterial to the functioning of the sensing device 18 which individual fibers of the sensing cable 8 transmit light to the sensing device 18 and which transmit it back, the plug connector 30 and the plug connector 40 can be rotated inside the plug-in connector 2 in any way desired. Thus, one need not adhere to any particular torsional position, even when inserting the plug connectors 30 and 40. Consequently, the plug-in connector 2 is especially easy to manipulate.

It is understood that the present invention is not limited to the embodiments shown in FIGS. 1 to 4. For instance, the hybrid cable and the sensing cable could be optically coupled in a detachable plug-in connector comprising a plug connector for one of the two cables and a socket connector receiving said plug connector for the other cable. The optically coupled ends of the hybrid cable and the sensing cable are preferably rotationally symmetric to provide a connection invariant to rotation of the plug connector with respect to the socket connector.

What is claimed is:

1. An optical fiber measuring arrangement including an optical transmitter, an optical receiver and an optical sensing device, comprising:
   (a) a transmitting bundle having a plurality of individual fibers capable of transporting light emanating from the optical transmitter;
   (b) a receiving bundle having a plurality of individual fibers capable of transporting light to the optical receiver;
   (c) a sensing cable having a plurality of individual fibers capable of transporting light to and from the optical sensing device, wherein light transmitted to the optical sensing device by said sensing cable is capable of being modulated in accordance with a measured variable and the modulated light is transmitted from the optical sensing device by said sensing cable;
   (d) a detachable plug-in connector, including:
      (i) a hybrid cable including a combination of said transmitting bundle and said receiving bundle, wherein in an end area of said hybrid cable all of the plurality of individual fibers of said transmitting bundle are arranged at least a predetermined distance from all of the plurality of individual fibers of said receiving bundle, with the predetermined distance having a magnitude at least at as large as the diameter of a largest individual fiber; and
      (ii) an optical coupler coupling said end area of said hybrid cable and said sensing cable.

2. The optical fiber measuring arrangement of claim 1 wherein said hybrid cable includes a crosspiece capable of separating said transmitting bundle and said receiving bundle.

3. The optical fiber measuring arrangement of claim 1 wherein said hybrid cable includes an internal cladding capable of separating said transmitting bundle from said receiving bundle, said internal cladding positioned such that said transmitting bundle and said receiving bundle reside in a substantially coaxial orientation within said hybrid cable.

4. The optical measuring arrangement of claim 1 wherein
   a) said sensing bundle exhibits a circular cross-section, at least in the area of an end of said sensing bundle nearest said detachable plug-in connector,
   b) said hybrid cable exhibits a circular cross-section, at least in the area of an end of said hybrid cable nearest said detachable plug-in connector,
   c) with the center of said circular cross-section of said sensing bundle and the center of said circular cross-section of said hybrid cable lying on an axis which is orthogonal to both cross-sections.

5. The optical measuring arrangement of claim 2 wherein
   a) said sensing bundle exhibits a circular cross-section, at least in the area of an end of said sensing bundle nearest said detachable plug-in connector, b) said hybrid cable exhibits a circular cross-section, at least in the area of an end of said hybrid cable nearest said detachable plug-in connector, c) with the center of said circular cross-section of said sensing bundle and the center of said circular cross-section of said hybrid cable lying on an axis which is orthogonal to both cross-sections.

6. The optical measuring arrangement of claim 3 wherein
   a) said sensing bundle exhibits a circular cross-section, at least in the area of an end of said sensing bundle nearest said detachable plug-in connector,
   b) said hybrid cable exhibits a circular cross-section, at least in the area of an end of said hybrid cable nearest said detachable plug-in connector,
   c) with the center of said circular cross-section of said sensing bundle and the center of said circular cross-section of said hybrid cable lying on an axis which is orthogonal to both cross-sections.

7. In an optical fiber measuring device comprising an optical sensor, an optical transmitter, and an optical receiver, a detachable plug-in connector comprising:
   (a) a transmitting bundle having a plurality of individual fibers capable of transporting light emanating from the optical transmitter;
   (b) a receiving bundle having a plurality of individual fibers capable of transporting light to the optical receiver;
   (c) a sensing cable having a plurality of individual fibers capable of transporting light to and from the optical sensor, wherein light transmitted to the optical sensor by said sensing cable can be modulated in accordance with a measured variable and the modulated light is transmitted from the optical sensor by said sensing cable;
   (d) a hybrid cable including a combination of said transmitting bundle and said receiving bundle, wherein said hybrid cable is capable of separating said transmitting bundle and said receiving bundle by a predetermined distance from one another with said predetermined distance having a magnitude at least as large as the diameter of a largest fiber;
   (e) a first plug connector detachably securing said hybrid cable to said detachable plug-in connector;
   (f) a second plug connector detachably securing said sensing cable to said detachable plug-in connector; and
   (g) a centerpiece positioning said first and second plug connectors such that said hybrid cable and said sensing cable are optically coupled.

8. The detachable plug-in connector of claim 7 wherein said hybrid cable includes a crosspiece capable of separating said transmitting bundle from said receiving bundle.

9. The detachable plug-in connector of claim 7 wherein said hybrid cable includes an internal cladding capable of separating said transmitting bundle from said receiving bundle, said internal cladding positioned such that said transmitting bundle and said receiving bundle reside in a substantially coaxial orientation within said hybrid cable.

10. The detachable plug-in connector of claim 8 wherein
    (a) said sensing bundle exhibits a circular cross-section, at least in the area of an end of said sensing bundle nearest said detachable plug-in connector, and
    (b) said hybrid cable exhibits a circular cross-section, at least in the area of an end of said hybrid cable nearest said detachable plug-in connector.

11. The detachable plug-in connector of claim 9 wherein
    (a) said sensing bundle exhibits a circular cross-section, at least in the area of an end of said sensing bundle nearest said detachable plug-in connector, and
    (b) said hybrid cable exhibits a circular cross-section, at least in the area of an end of said hybrid cable nearest said detachable plug-in connector.

12. In an optical fiber measuring device including an optical sensor, a sensing cable, an optical transmitter, a transmitting bundle, an optical receiver and a receiving bundle, with the sensing cable, the transmitting bundle and the receiving bundle each having a plurality of individual fibers capable of transporting light, a detachable plug-in connector comprising:
    (a) a first plug connector including a first end capable of securing the transmitting bundle and the receiving bundle to said first plug connector, wherein the transmitting bundle and the receiving bundle are separated from one another, by a predetermined distance being at least as large as the diameter of a largest individual fiber and a second end capable of detachably securing said first plug connector to said detachable plug-in connector;
    (b) a second plug connector including a first end capable of securing the sensing cable to said second plug connector, and a second end capable of detachably securing said second plug connector to said detachable plug-in connector; and
    (c) a centerpiece for positioning said first and second plug connectors such that the transmitting bundle and the receiving bundle are optically coupled to the sensing cable.

13. The detachable plug-in connector of claim 12 wherein said first plug connector includes a crosspiece capable of separating the transmitting bundle from the receiving bundle.

14. The detachable plug-in connector of claim 12 wherein said first plug connector includes an internal cladding capable of separating the transmitting bundle from the receiving bundle, said internal cladding positioned such that the transmitting bundle and the receiving bundle reside in a substantially coaxial orientation within said first plug connector.

* * * * *